US00PP36080P3

(12) United States Plant Patent
Essner et al.

(10) Patent No.: US PP36,080 P3
(45) Date of Patent: Aug. 27, 2024

(54) APPLE TREE NAMED 'SF118'

(50) Latin Name: *Malus domestica*
Varietal Denomination: SF118

(71) Applicant: The New Zealand Institute for Plant and Food Research Limited, Auckland (NZ)

(72) Inventors: Bruno Essner, Angers (FR); Kenneth Charles Breen, Hastings (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 50 days.

(21) Appl. No.: 17/803,704

(22) Filed: Oct. 14, 2022

(65) Prior Publication Data

US 2023/0189676 P1 Jun. 15, 2023

Related U.S. Application Data

(60) Provisional application No. 63/273,696, filed on Oct. 29, 2021.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ... A01H 5/08; A01H 5/00; A01H 6/74; A01H 6/7418
See application file for complete search history.

(56) References Cited

U.S. PATENT DOCUMENTS

PP34,399 P2 * 7/2022 Breen ..... Plt./161

* cited by examiner

*Primary Examiner* — June Hwu
(74) *Attorney, Agent, or Firm* — Leydig, Voit & Mayer, LTD.

(57) ABSTRACT

A new and distinct variety of apple tree is described. The variety results from a limb sport found in Angers, France. The fruit of the apple tree of this new variety have an attractive appearance, characterised by a high proportion of red over color and an over color pattern that is a solid flush.

5 Drawing Sheets

Genus and species plant named: *Malus domestica.*
Variety denomination: 'SF118'.

BACKGROUND OF THE INVENTION

The new variety of apple tree 'SF118', *Malus domestica*, resulted from a spontaneous limb sport mutation of 'Scifresh' (U.S. Plant Pat. No. 13,888). The 'Scifresh' tree containing the limb sport of the new variety was discovered in 2012, growing in a cultivated commercial test block in Angers, France. It was selected for further observation because of its fruit skin over color. It was originally given the code SF118-29 but later named 'SF118'. 'SF118' was first asexually propagated in 2012 in Angers, France by budding onto 'M9' rootstock. The grafted trees were planted in an orchard in 2014. The resulting plants were found to be true to type demonstrating that the characteristics of the new variety 'SF118' are stable and transmitted without change through succeeding generations.

SUMMARY OF THE INVENTION

The new and distinct 'SF118' variety is characterised by its medium sized fruit and skin over color and pattern. The over color is red (near dark red 46B), the relative area of the over color large and the over color pattern a solid flush.

'SF118' is distinguished from its parent, 'Scifresh' by the following characteristics.

'SF118' has on average a higher percentage of the fruit skin color (83%) compared to 'Scifresh' 73%. In addition, 'SF118''s over color pattern is solid flush compared to 'Scifresh' which is solid flush with narrow, weakly defined stripes.

BRIEF DESCRIPTION OF DRAWINGS

The accompanying photographs show typical specimens of the tree, foliage and fruit of the new variety as depicted in colors as nearly true as is reasonably possible to make the same in a color illustration of this character.

DETAILED DESCRIPTION

Figure 1:
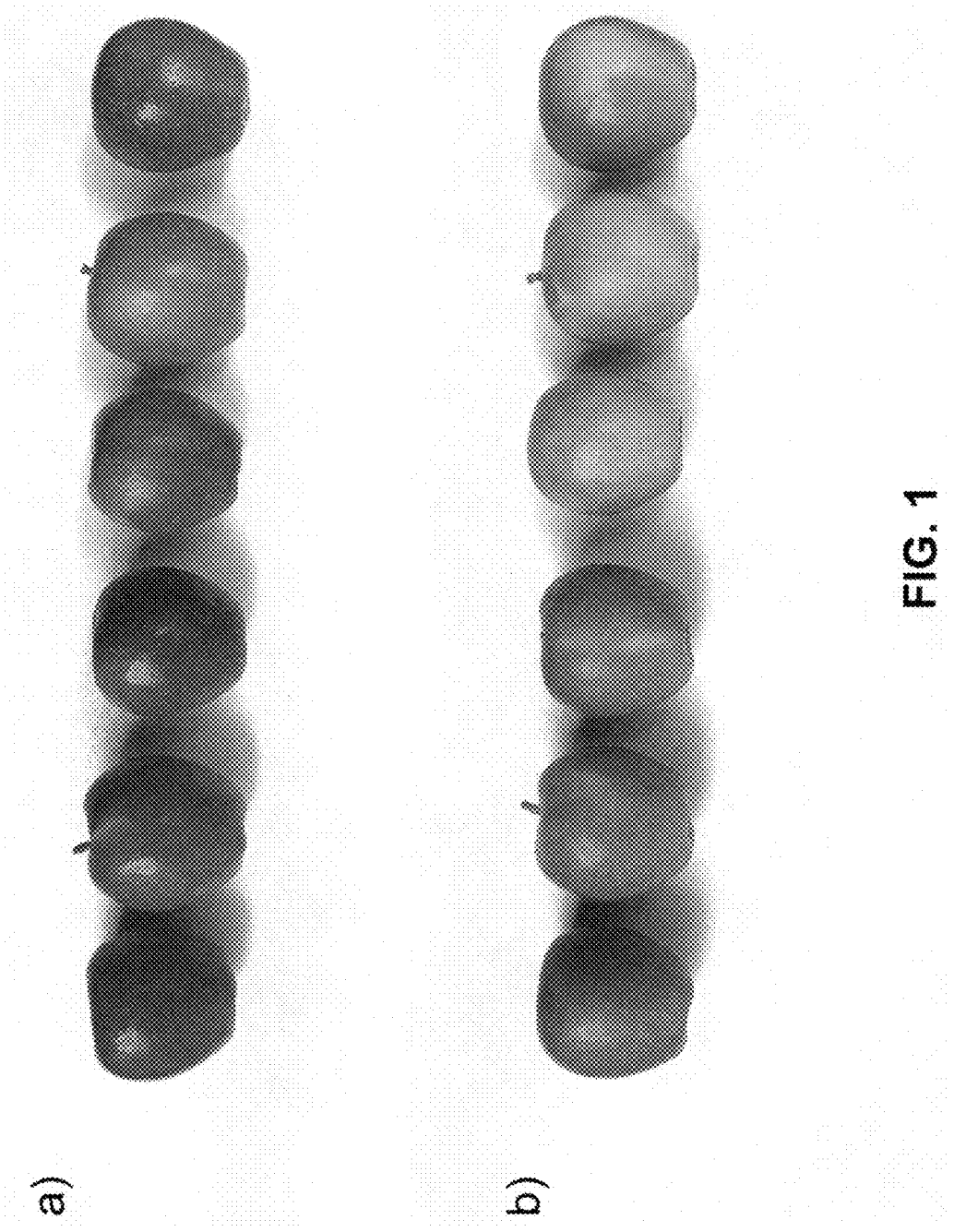
FIG. 1: 'SF118' fruit lateral views of a) highly colored fruit side and b) lower colored fruit side of the same fruit.
Figure 2:
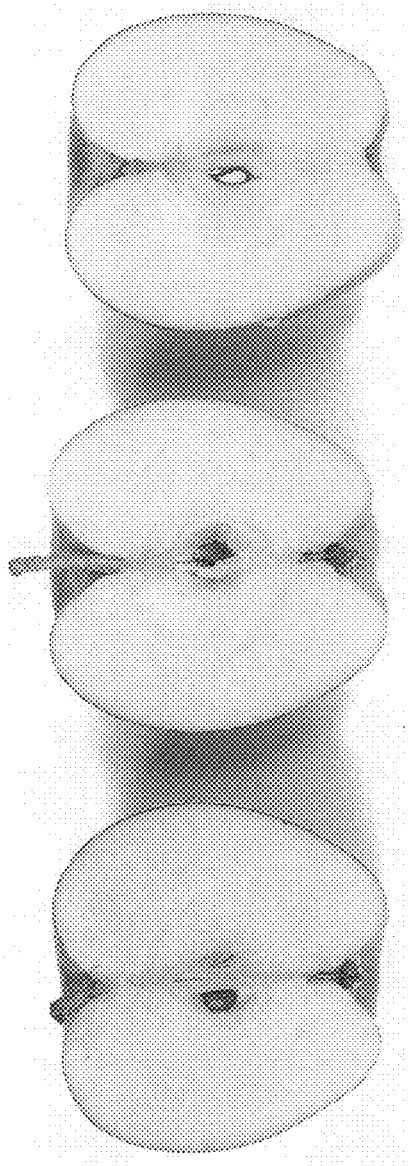
FIG. 2: 'SF118' longitudinal section of cut fruit.
Figure 3:
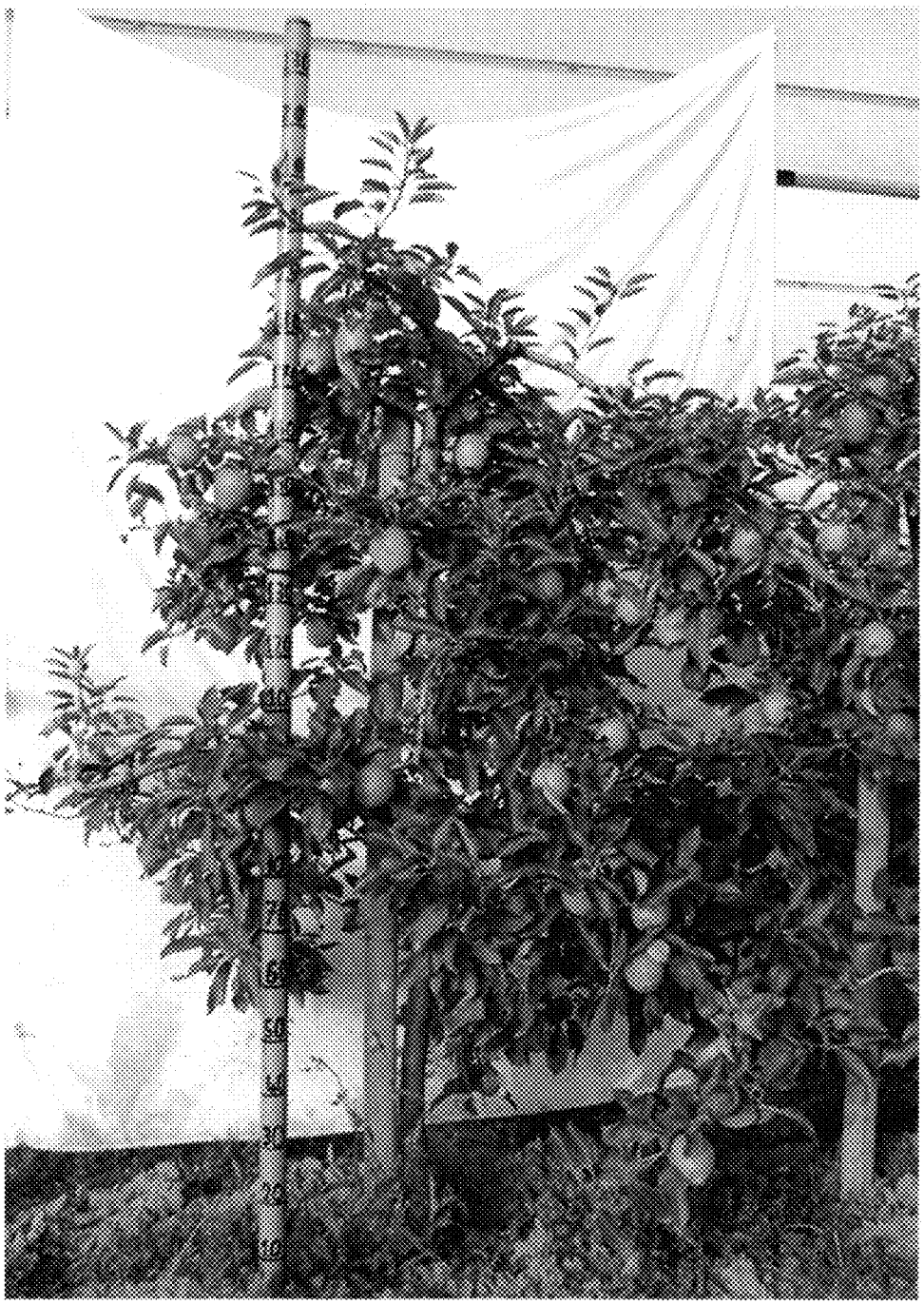
FIG. 3: 'SF118' 5-year-old tree.
Figure 4:
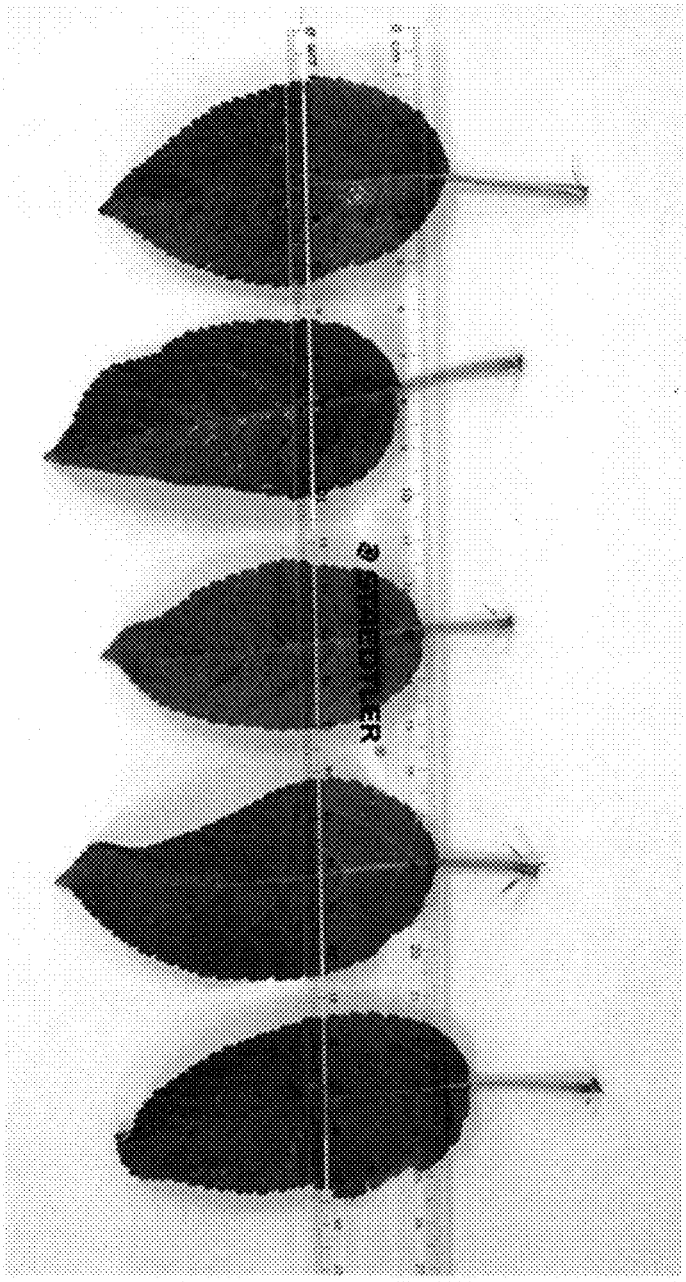
FIG. 4: 'SF118' top side of leaves.
Figure 5:
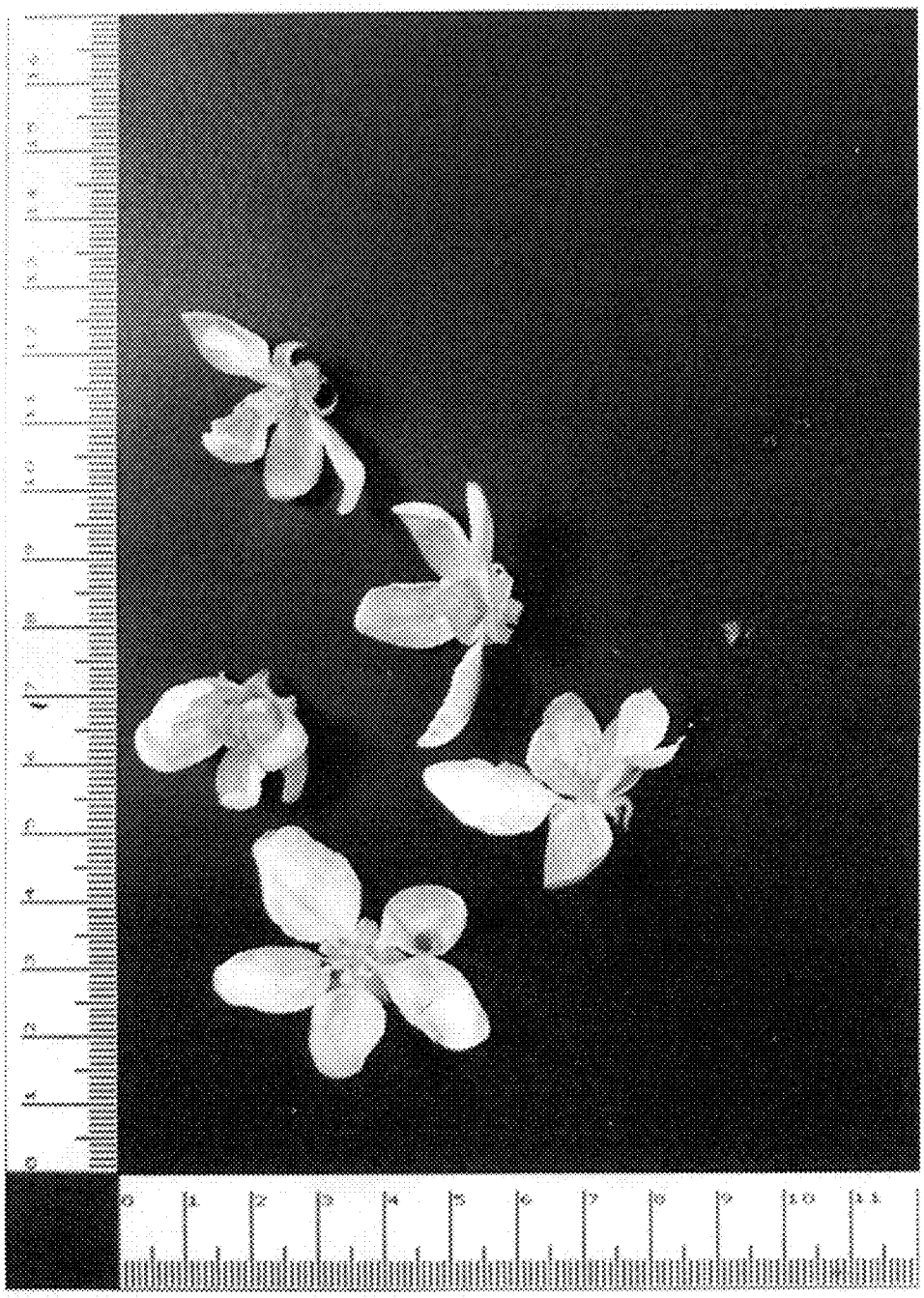
FIG. 5: 'SF118' flowers.

The following is a description of the new variety with color terminology in accordance with The UPOV Colour Chart (TGP/14/6, Section 2, Subsection 3: Colour) and The Royal Horticultural Society Colour Chart (R.H.S.C.C.) 2015 edition. Observations made on trees in Angers, France; over two seasons, 2019 and 2020, aged 5-6 years on 'M9' rootstock. Measurements and observations taken from the five trees or plant parts taken off each of the five trees.

Tree:
*Size*.—Average height 2.44 m, average width 1.68 m.
*Type*.—Ramified.
*Habit*.—Spreading.
*Vigour*.—Medium to strong on 'M9', managed under standard orchard practices.
*Bearing*.—On spurs and long shoots.
Trunk:
*Size*.—Average circumference 20 cm above the graft union 15.9 cm.
*Bark texture*.—Slightly rough.
*Bark color*.—Near dark grey, 197C.
One-year-old shoot:
*Growth*.—Straight.
*Thickness*.—Medium, average 5-6 mm.
*Length of internode*.—Medium, average 20 mm.
*Length of shoot*.—Average 294 mm.
*Predominant color on sunny side*.—Near medium brown, 200A.
*Pubescence on distal half of the shoot*.—Medium.
*Number of lenticels*.—Medium, average 7 per cm2.
*Lenticel shape*.—Elliptical to irregular round.
*Lenticel size*.—Average length 1 mm, average width 1 mm.
*Lenticel color*.—Near light grey, 156C.
Vegetative bud:
*Shape of apex of vegetative bud*.—Acute.
*Position of vegetative bud in relation to shoot*.—Adpressed to slightly held out.
*Vegetative bud length*.—Average 7 mm.
*Vegetative bud color*.—Near dark brown, 200A.
Leaf blade:
*Attitude in relation to shoot*.—Outwards.
*Length*.—Medium, average 78 mm.
*Width*.—Medium, average 40 mm.
*Ratio length/width*.—Medium.
*Shape of base*.—Obtuse.
*Shape of apex* (*excluding pointed tip*).—Acute.
*Intensity of green color*.—Medium.
*Incisions of margin* (*upper half*).—Crenate.
*Lower surface pubescence*.—Weak.
*Upper surface color*.—Near dark brown green, 147A.
*Lower surface color*.—Near medium brown green, 148C.
*Venation color*.—Near medium grey green, 145C.
Petiole:
*Petiole length*.—Medium, average 26 mm.
*Petiole width*.—Average 3 mm.
*Petiole upper color*.—Near light green, 139D.
*Petiole lower color*.—Near medium grey green, 145C.
*Extent of anthocyanin coloration from base*.—Medium.
*Presence of stipules*.—Present.
*Stipule length*.—Average 4 mm.
*Stipule width*.—Average 1 mm.
*Stipule upper color*.—Near medium brown green, 147B.
*Stipule lower color*.—Near light green, 138C.
Flower:
*Predominant color at balloon stage*.—Near red pink, 53C.
*Diameter with petals pressed into horizontal*.—Medium, average 39 mm.
*Arrangement of petals*.—Intermediate.
*Position of stigmas relative to anthers*.—Above.
*Location of flower bud*.—Mainly on spurs.
*Average number of buds per spur*.—1.2.
*Average number of flowers per cluster*.—5.
*Average number of sepals/flower*.—5.
*Sepal length*.—Medium, average 7 mm.
*Sepal width*.—Average 4 mm.
*Sepal color*.—Near light green, 145A.
*Attitude of sepals in relation to corolla*.—Recurved.
*Average number of petals/flower*.—5.
*Size of petal*.—Average length 18 mm, average width 11 mm.
*Shape of petal* (*excluding the claw*).—Ovate.
*Shape of base of petal* (*excluding the claw*).—Rounded.
*Length of claw of petal*.—Average 2 mm.
*Petal color on lower side*.—Near medium purple red, 61C.
*Petal venation color on lower side*.—Near medium purple 71B.
*Petal color on upper side*.—White, NN155C.
*Petal venation color on upper side*.—Near medium purple 71B.
*Average number of stamen per flower*.—19.
*Average filament length*.—5 mm.
*Filament color*.—Near white, 155D.
*Average anther length*.—3 mm.
*Average anther width*.—1 mm.
*Anther color*.—Near light yellow, 4D.
*Pollen color*.—Near medium yellow, 7D.
*Average pistil length*.—9 mm.
*Pistil color*.—Near light Green, 145B.
*Average pedicel length*.—17 mm.
*Average pedicel width*.—2 mm.
*Pedicel color*.—Near dark green brown, 152B.
*Fragrance*.—Present.
Young fruit:
*Extent of anthocyanin*.—Small.
Fruit size:
*Size*.—Medium, average weight 206 g.
*Height*.—Medium, average 74 mm.
*Diameter*.—Medium, average 74 mm.
*Position of maximum diameter*.—Middle.
Fruit shape:
*General shape*.—Conic to globose, most fruit tending towards being conic.
*Position of maximum diameter*.—Middle.
*Ribbing*.—Absent or weak.
*Crowning at calyx end*.—Absent or weak.
*Size of eye*.—Small to medium.
*Length of sepal*.—Medium, average 4 mm.
*Depth of eye basin*.—Medium, average 11 mm.
*Width of eye basin*.—Medium, average 29 mm.
Fruit skin:
*Bloom of skin*.—Absent or weak.
*Greasiness of skin*.—Absent or weak.
*Ground color of skin*.—Near medium yellow, 2A.
*Relative area of over color*.—Large, average 83%.
*Hue of over color*.—With bloom removed — Near dark red, 46B.
*Intensity of over color*.—Medium.
*Pattern of over color*.—Only solid flush.
*Area of russet around stalk attachment*.—Absent.
*Area of russet on cheeks*.—Absent.

*Area of russet around eye basin*.—Absent.
*Size of lenticels*.—Small.
*Surface texture of skin*.—Smooth.

Fruit stalk:
*Length of stalk*.—Medium, average 19 mm.
*Thickness of stalk*.—Medium, average 4 mm.
*Depth of stalk cavity*.—Medium, average 14 mm.
*Width of stalk cavity*.—Medium, average 32 mm.

Fruit flesh:
*Firmness of flesh*.—Firm, average 9.6 kgf.
*Color of flesh*.—Yellowish, near 158A.
*Aperture of locules* (*in transverse section*).—Closed or slightly open.
*Texture of flesh*.—Medium.
*Water-core of flesh*.—Absent to very weak.

Fruit flavour: Medium sweetness, average soluble solids, 13% brix, medium acidity.

Fruit seeds:
*Average number of locules*.—5.
*Seed shape*.—Ovate.
*Average seed length*.—9 mm.
*Average seed width*.—5 mm.
*Average seed weight*.—0.06 g.
*Seed color*.—Near medium brown, 175A.

Event timing:
*Time of beginning of flowering*.—Medium, mid May, similar to 'Scifresh'.
*Time for harvest*.—Late, late September, similar to 'Scifresh'.
*Time of eating maturity*.—Medium to late.
*Storage quality*.—Keeping quality is excellent, up to 8 months at 0.5° C., with 1 week shelf life.

Plant hardiness zone and disease pest resistance: The plant hardiness zone is 6a, 6b, 7a, and 7b. No plant or fruit disease, or pest resistance/susceptibility has been observed to date.

Table 1: Comparison table between the similar varieties 'Scifresh' (parent), 'SF1' (U.S. Plant Pat. No. 34,399) and the candidate variety 'SF118'. Observations made on trees in Angers, France; over 2 seasons, 2019 and 2020, on 'M9' rootstock.

| Characteristic | 'Scifresh' | 'SF1' | 'SF118' |
|---|---|---|---|
| Relative area of over color | Medium, average 73% | Very Large, average 96% | Large, average 83% |
| Pattern of over color | Solid flush with narrow, weakly defined stripes | Solid flush with narrow, weakly defined stripes | Only solid flush |
| Over color hue with bloom removed | Near 42D | Near 53A | Near 46B |
| Ground color of Skin | Yellow green, Near 154D | Yellow, Near 4A | Yellow, Near 2C |

The invention claimed is:

1. A new and distinct variety of apple tree named 'SF118' substantially as illustrated and described herein.

* * * * *